US006876881B2

(12) United States Patent
Baumann et al.

(10) Patent No.: US 6,876,881 B2
(45) Date of Patent: Apr. 5, 2005

(54) CARDIAC RHYTHM MANAGEMENT SYSTEM WITH RESPIRATION SYNCHRONOUS OPTIMIZATION OF CARDIAC PERFORMANCE USING ATRIAL CYCLE LENGTH

(75) Inventors: Lawrence S. Baumann, Bloomington, MN (US); Veerichetty A. Kadhiresan, Temecula, CA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 425 days.

(21) Appl. No.: 10/222,153

(22) Filed: Aug. 16, 2002

(65) Prior Publication Data

US 2004/0034391 A1 Feb. 19, 2004

(51) Int. Cl.$^7$ ............................................. A61N 1/365
(52) U.S. Cl. ............................ 607/18; 607/20; 607/25
(58) Field of Search ........................ 607/9, 15, 17–20, 607/24, 25

(56) References Cited

U.S. PATENT DOCUMENTS 5,540,727 A   7/1996   Tockman et al. ............. 607/18
5,800,471 A   9/1998   Baumann ..................... 607/25

*Primary Examiner*—Carl Layno
(74) *Attorney, Agent, or Firm*—Thomas J. Nikolai; Nikolai & Mersereau, P.A.

(57) ABSTRACT

A cardiac rhythm management device includes a dual chamber pacemaker, especially designed for treating congestive heart failure. The device incorporates a program microcontroller which is operative to adjust the pacing site, AV delay and interventricular delay of the pacemaker so as to achieve optimum hemodynamic performance. Atrial cycle lengths measured during transient (immediate) time intervals following a change in the site, AV delay and interventricular delay are signal processed and a determination can then be made as to which particular configuration yields the optimum performance. Paced transient beats following periods of baseline beats are synchronized to the patient's respiratory cycle to minimize effects of respiratory noise on atrial cycle length measurements.

9 Claims, 7 Drawing Sheets

- INTRINSIC OR PACED BASELINE BEATS.
- PACED TRANSIENT BEATS.

CARDIAC RHYTHM MANAGEMENT SYSTEM WITH RESPIRATION SYNCHRONOUS OPTIMIZATION OF CARDIAC PERFORMANCE USING ATRIAL CYCLE LENGTH

BACKGROUND OF THE INVENTION

I. Field of the Invention

This invention relates generally to implantable cardiac rhythm management devices, and more particularly to a method for establishing optimum pacing site and intersite delay (i.e., AV delay and interventricular delay) parameters for a dual chamber implantable programmable pacemaker.

II. Discussion of the Prior Art

As is explained in the Baumann Patent 4,800,471 and co-pending application Ser. Nos. 09/545,536 and 09/734,282, assigned to the assignee of the present invention, and the teachings of which are hereby incorporated by reference, it is explained that cardiac pacing can be used to improve hemodynamics in congestive heart failure (CHF) patients. One indication of hemodynamic performance is reflected in the patient's pulse pressure (PP) which is defined as the difference between peak systolic aortic pressure and end diastolic aortic pressure. While PP could be used to optimize the pacing parameters in applying CHF therapy, a direct measure of PP would require the use of a suitably positioned pressure sensor inside the heart.

As is explained in the aforereferenced Baumann '471 patent and co-pending applications, an indirect indication of PP can be derived from the patient's atrial cycle length (ACL), which is the duration of the interval between consecutive P-waves in an ECG signal. The method disclosed in the above-cited patent/applications for using ACL to optimize CHF therapy parameters involves looking at a transient sequence in which, after a period of intrinsic cardiac activity, a short sequence of pacing stimuli is delivered to the patient's heart. Any subsequent transient increase in measured ACL provides an indication of the therapy's effectiveness over intrinsic cardiac activity. Likewise, a subsequent transient decrease in measured ACL is indicative that the pacing therapy is non-beneficial.

In applying the methodology to an implantable, microprocessor-based controller of the type typically used in a programmable dual-chamber pacemaker, the device is made to cycle through transient paced beats with different pacing site and AV delay configurations. Each such configuration is defined to be a group of consecutive beats with the same paced intersite delay and the same pacing site (right ventricular, left ventricular or biventricular pacing). As used herein, term "intersite delay" means the time interval between any sequential pacing events in the same cardiac cycle, regardless of whether they occur in different or in the same chamber. Each of the configurations is immediately preceded by a group of baseline beats. In the disclosed arrangement, three different pacing sites and five different intersite delays are used, with the AV delay of each such intersite delay being shorter than a previously measured value of the intrinsic AV delay. During bi-ventricular pacing, various interventricular delays are also tested. Interventricular delays provide variations in time intervals between pulse events with respect to pacing at multiple sites. It is common to stimulate both ventricle chambers, for example, and particularly the left ventricle can be provided with a plurality of sequentially paced beats. Each of these is operated using a timed delay sequence, which may be selected from a menu of sequence timings. The particular site and intersite delay configuration that results in the largest increase in ACL is then programmed into the pacemaker to thereby optimize hemodynamic performance of the patient's heart.

To avoid inaccuracies due to noise, the algorithm described in the Baumann '471 patent is made to vary the order of therapy randomization and averaging techniques are then used to extract data from repeated tests. While this approach has the effect of nulling out noise components, we have found that a significant portion of the unwanted noise in the ACL signal is due to respiration artifacts. To minimize the impact of respiration on hemodynamic parameters, such as ACL, in accordance with the present invention, the algorithm utilized in the Baumann '471 patent and the cited co-pending applications is modified. First, a respiration signal is derived, and then, on each iterative cycle when pacing pulses are applied following a period of intrinsic (baseline) cardiac activity, the delivery of the sequence of pacing pulses is synchronized to a predetermined phase of the derived respiration signal. Moreover, each test combination of pacing site and intersite delay uses pacing stimuli that are synchronized to the same phase of the respiration cycle. In doing so, noise due to respiration artifacts is essentially eliminated. As such, superior optimization of therapy parameters and improved hemodynamic performance are achieved. Further, by synchronizing the pacing pulses to the respiration waveform, a shortened testing and optimization protocol is made possible: Fewer repeated tests are required to obtain, after averaging, a specified noise level, since the noise due to respiration is reduced.

SUMMARY OF THE INVENTION

The foregoing features and advantages of the invention are achieved by providing an improved method for optimizing the intersite delay and pacing site configuration of an implanted, programmable pacemaker when treating CHF patients. The pacemaker involved is of the dual chamber type that includes an atrial sense circuit, a ventricular sense circuit and a pulse generator for applying cardiac stimulating pulses selectively to the right ventricular chamber, the left ventricular chamber or both chambers simultaneously (biventricular pacing). The pacemaker may also include a known circuit arrangement for measuring transthoracic impedance and for deriving therefrom an electrical signal proportional to the patient's tidal volume. The patient's intrinsic atrial depolarization events are tracked and from such events the ACL is measured over a first predetermined number of heartbeats, $N_1$, to establish a baseline value. At least one of the intersite delay interval and the pacing site configuration is changed for a predetermined number of stimulated heartbeats, $N_2$, and, again, the ACLs between successive paced beats are measured. These steps are repeated in iterative cycles until all of the preprogrammed intersite delay intervals and ventricular chamber options have been utilized. On each iterative cycle, the pacing stimuli are applied in synchronization with the tidal volume signal such that the stimulating pulses begin at the same phase of the respiratory cycle. Subsequently, a comparison is made to determine which pacing site and intersite delay value resulted in the maximum ACL, and those values are then programmed into the pacemaker. In that maximum ACL correlates with maximum PP, hemodynamic performances are thereby optimized.

DESCRIPTION OF THE DRAWINGS

The foregoing features, objects and advantages of the present invention will become apparent to those skilled in the art from the following detailed description of a preferred embodiment, especially when considered in conjunction with the accompanying drawings in which.

DESCRIPTION OF THE PREFERRED EMBODIMENT

Figure 1:
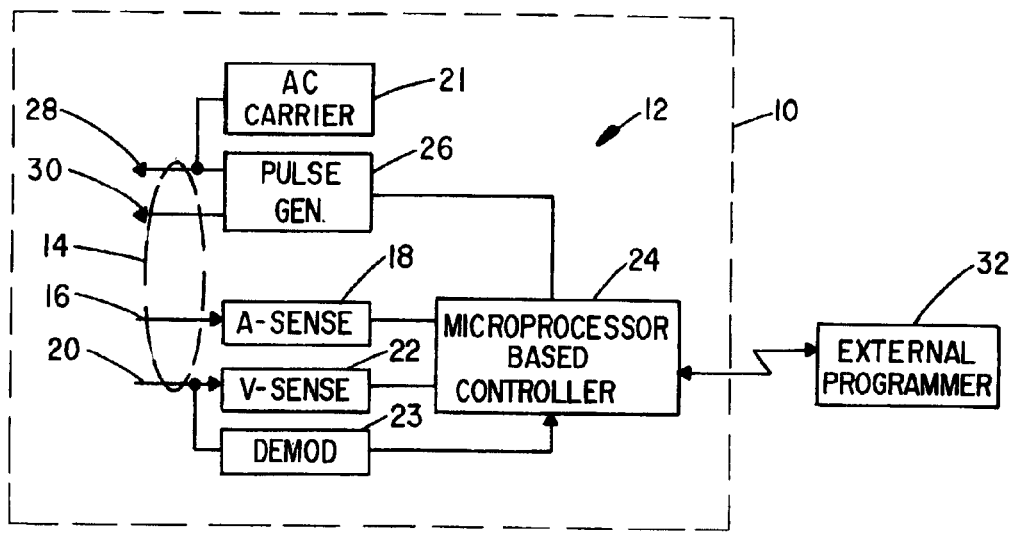
FIG. 1 is a schematic block diagram of a dual chamber pacemaker incorporating a microprocessor-based controller in which the intersite delay parameters are optimized in accordance with the algorithm disclosed herein.

Referring first to FIG. 1, there is shown enclosed by a dashed-line box 10, a cardiac rhythm management device, here depicted as a VDD bradycardia pacemaker 12, which is adapted to be operatively coupled to a patient's heart by means of a conventional pacing lead 14. In the VDD mode, sensed atrial activity triggers ventricular pacing after completing the programmed intersite delay interval. In particular, an atrial sensing electrode disposed in the right atrium of the heart is coupled by a wire 16 in the lead 14 to an atrial sense amplifier 18. Similarly, a ventricular sensing electrode disposed in the right ventricle is connected by a wire 20 in the lead 14 to a ventricular sense amplifier 22 contained within the pacemaker 12. Thus, when the SA node in the right atrium depolarizes, the resulting signal is picked up by the atrial sense amplifier 18 and applied to a microprocessor-based controller 24 which will be more particularly described with the aid of FIG. 2. Ventricular depolarization signals (R-waves) are likewise amplified by the ventricular sense amplifier 22 and applied as an input to the microprocessor-based controller 24.

To obtain a signal proportional to the patient's tidal volume, circuitry for detecting variation in transthoracic impedance is also included. Specifically, a source 21 of an AC carrier signal is connected across a pair of electrodes on the lead 14 and that carrier signal is modulated by the patient's respiratory activity. The modulated carrier is demodulated in demodulator circuit 23 with the envelope being digitized and delivered to microprocessor-based controller 24. Details for deriving a respiratory signal from transthoracic impedance can be obtained from a reading of the Hauck Patent 5,318,597.

The microprocessor-based controller 24 is connected in controlling relationship to a pulse generator 26 to cause a ventricular stimulating pulse to be applied, via conductor 28 in lead 14, to tissue located proximate the apex of the right ventricle (RV) to initiate ventricular depolarization that spreads as a wave across both the right and left ventricles. The pulse generator 26, under control of the microprocessor-based controller 24, can also be made to apply stimulating pulses over a wire 30 in lead 14 to stimulate the heart's left ventricle (LV). If the pacing site calls for biventricular pacing, the pulse generator 26 is controlled by the microprocessor-based controller 24 to deliver stimulating pulses to both the right and left ventricles (BV).

The microprocessor-based controller 30 not only controls the rate at which cardiac stimulating pulses are produced, but also the timing thereof relative to a preceding atrial depolarization signal to thereby define intersite delay intervals (AV delay and interventricular delays).

An external programmer 32 is arranged to send data signals transcutaneously to the implanted pacemaker 12 and also to receive signals originating within the pacemaker. In this fashion, a physician is capable of programming such parameters as pacing rate, pacing pulse width, pacing pulse amplitude, sensitivity, intersite delay intervals, etc., in a fashion known in the art. The external programmer may also be used to receive signals and pass them on to an external monitor (not shown) incorporating a microprocessor and associated memory.

Figure 2:
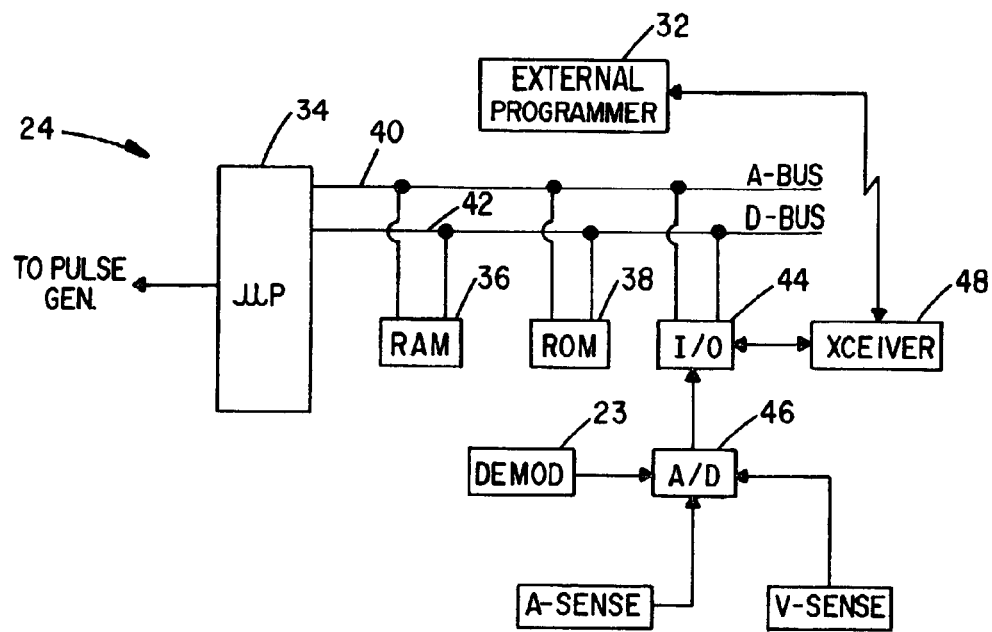
FIG. 2 is a schematic block diagram of the microprocessor-based controller incorporated into the pacemaker of FIG. 1.

FIG. 2 shows a more detailed block diagram of the microprocessor-based controller 24 shown in FIG. 1. It is conventional in its architecture and includes a microprocessor chip 34 and associated RAM and ROM memory modules 36 and 38 connected to it by an address bus 40 and a data bus 42. As is known in the art, the RAM memory 36 is a read/write memory comprising a plurality of addressable storage locations where multi-byte data words and operands used in the execution of one or more programs may be stored for subsequent readout. The ROM memory 38 will typically be used to store the control programs executable by the microprocessor chip 34.

Also connected to the address bus and data bus is an I/O interface module 44. If a separate analog-to-digital converter, as at 46, is utilized rather than an on-board A/D converter forming a part of the microprocessor chip 34, its output will be connected through the I/O module 44 allowing the analog outputs from the atrial sense amplifier 18 and the ventricular sense amplifier 22 and the demodulator 23 to be digitized before being routed to the microprocessor chip 34. If the particular microprocessor employed incorporates an on-board A/D converter (as is somewhat conventional), then the outputs from the A-sense amplifier 18, V-sense amplifier 22 and the demodulator 23 would be applied directly to appropriate inputs of the microprocessor chip 34.

Also coupled to the I/O module 44 is a transceiver 48 that is used to interface the external programmer 32 to the implanted pacer 12. The manner in which an external programmer appropriately placed on the chest wall in proximity to the implanted device is capable of transmitting digitally encoded data therebetween is well known to those skilled in the pacemaker art.

Figure 3:
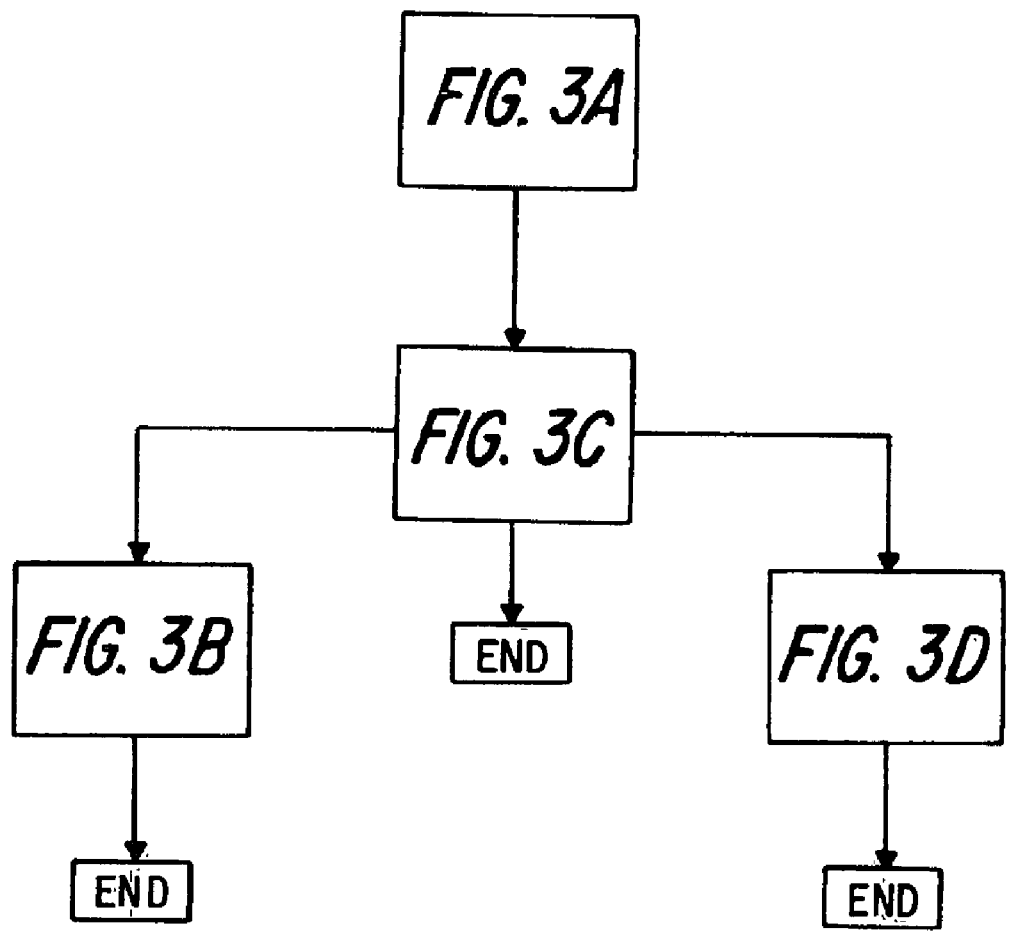
FIGS. 3A, 3B, 3C and 3D, when arranged as shown in FIG. 3, illustrate a flow diagram for the optimization algorithm of the present invention.

FIGS. 3A, 3B, 3C and 3D when arranged as shown in FIG. 3 comprise a flow chart of the algorithms executed by the microprocessor 34 in arriving at an optimal pacing site and intersite delay configuration for a patient in which the system of the present invention is implanted.

Before explaining the steps of the algorithm in detail, a brief overview of the methodology is deemed helpful.

The algorithms can be executed by the microprocessor-based controller in the pacer or in an external microprocessor in the monitor/programmer 32. In the following description, it is assumed that the control algorithms are executed by the microprocessor 34 in the implanted device. The algorithms, using cardiac atrial cycle lengths measured in the VDD pacemaker, determines a patient's optimum pacing site and intersite delay configuration, which is the site (e.g., RV, LV, or BV) and intersite delay during VDD pacing which maximizes cardiac function (e.g., PP) for the patient. The pulse generator 26 is then set to operate at this optimum pacing site and intersite delay configuration.

The optimal pacing mode-AV delay is determined from the maximum value of one of several empirically derived features, which are calculated from the atrial cycle lengths. In particular, the atrial cycle lengths immediately following a transition from an intrinsic or paced baseline (BL) to a paced site and intersite delay configuration, i.e., during a transient period of the paced site and intersite delay, is used. Thus, this invention eliminates the need for a period of waiting for hemodynamic stability to be reached during the paced site and intersite delay.

Figure 6:
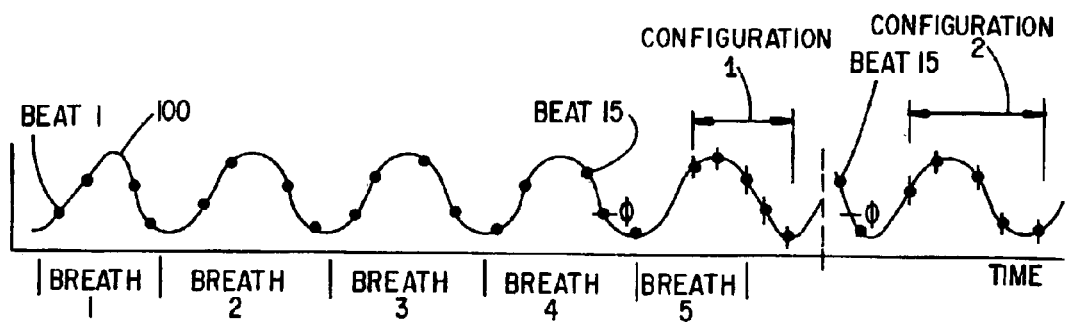
FIG. 6 is a respiratory waveform having intrinsic beats and paced beats marked thereon to illustrate the respiratory synchronization aspect of the present invention.

The pulse generator will be made to cycle through a predetermined number of intrinsic or paced BL beats followed immediately by paced beats using a first site and intersite delay configuration, followed immediately by additional intrinsic or paced BL beats, followed immediately by beats of a second site and intersite delay configuration, etc., until all of the possible configurations have been utilized. For each configuration, the initiation of the paced beats is synchronized to the tidal volume waveform derived from the demodulator 23. That is to say, the series of paced beats begins at the same phase of the tidal volume waveform as shown in FIG. 6. The ACL between successful beats is computed and stored as an array in the RAM memory of the microprocessor-based controller.

Once the array of ACL values is stored, they are subsequently processed to arrive at values of ACL features. In particular, the array of values may be smoothed using a 3-point moving rectangle window or an 11-point moving Blackman window. Then for each configuration and repeated instances thereof, further computations are made to identify the particular configuration exhibiting the largest average of the smoothed ACL features. It is this configuration that is determined to be the optimum and the pacemaker is then set to operate in this optimum configuration. The automatic selection of optimal site and intersite delay, which is found to optimize cardiac function eliminates any need for manual programming of the implanted pacemaker by the physician.

The algorithms of the present invention are based upon a hypothesis that if a transient change in atrial cycle length is large positive, then the preceding transient change in aortic pulse pressure was also large positive. Thus, the configuration with the largest positive change in atrial cycle length is hypothesized to be the configuration with the largest positive change in aortic pulse pressure.

There is a physiological basis for this relationship. A large, sudden increase in the aortic pressure (in this case due to the sudden change from baseline cardiac function to paced site and intersite delay configuration cardiac function) is sensed by arterial baroreceptors, and the reflex mechanism of the Autonomic Nervous System (ANS) tries to drive the aortic pressure back to its previous stable (in this case, baseline) value by increasing the atrial cycle length. The ANS acts as a negative feedback control system for the aortic pressure.

The paced site and intersite delay associated with the largest increase in ACL is hypothesized to be the optimum paced site and intersite delay for the pacemaker. The optimum is the one that provides a maximum increase in aortic pressure over baseline aortic pressure.

By synchronizing the initiation of the paced beats with the respiratory waveform, as illustrated in FIG. 6, the noise otherwise introduced in the ACL measurement due to respiratory activity is effectively eliminated.

With the foregoing summary in mind, then, attention is directed to the flow charts of FIGS. 3A through 3D. The first step in the algorithm is to derive a ventilatory signal proportional to the variation of transthoracic impedance due to respiration activity. See box 49. Next, as reflected in block 50 in FIG. 3A, the pulse generator is initially inhibited while intrinsic cardiac activity is sensed such that a value of the patient's intrinsic AV delay can be measured. Next, the physician may generate a list of all possible configurations of three pacing sites and a predetermined number of intersite delay values where each of the AV delay values is set to be less than the intrinsic AV value measured at block 50. While a different number of paced site and intersite delay values can be selected, for purposes of explanation of the inventive algorithm, it will be assumed that five different intersite delays with AV values less than the intrinsic value are established by the physician. This leads to 15 possible configurations as indicated in block 52.

Figure 3A:
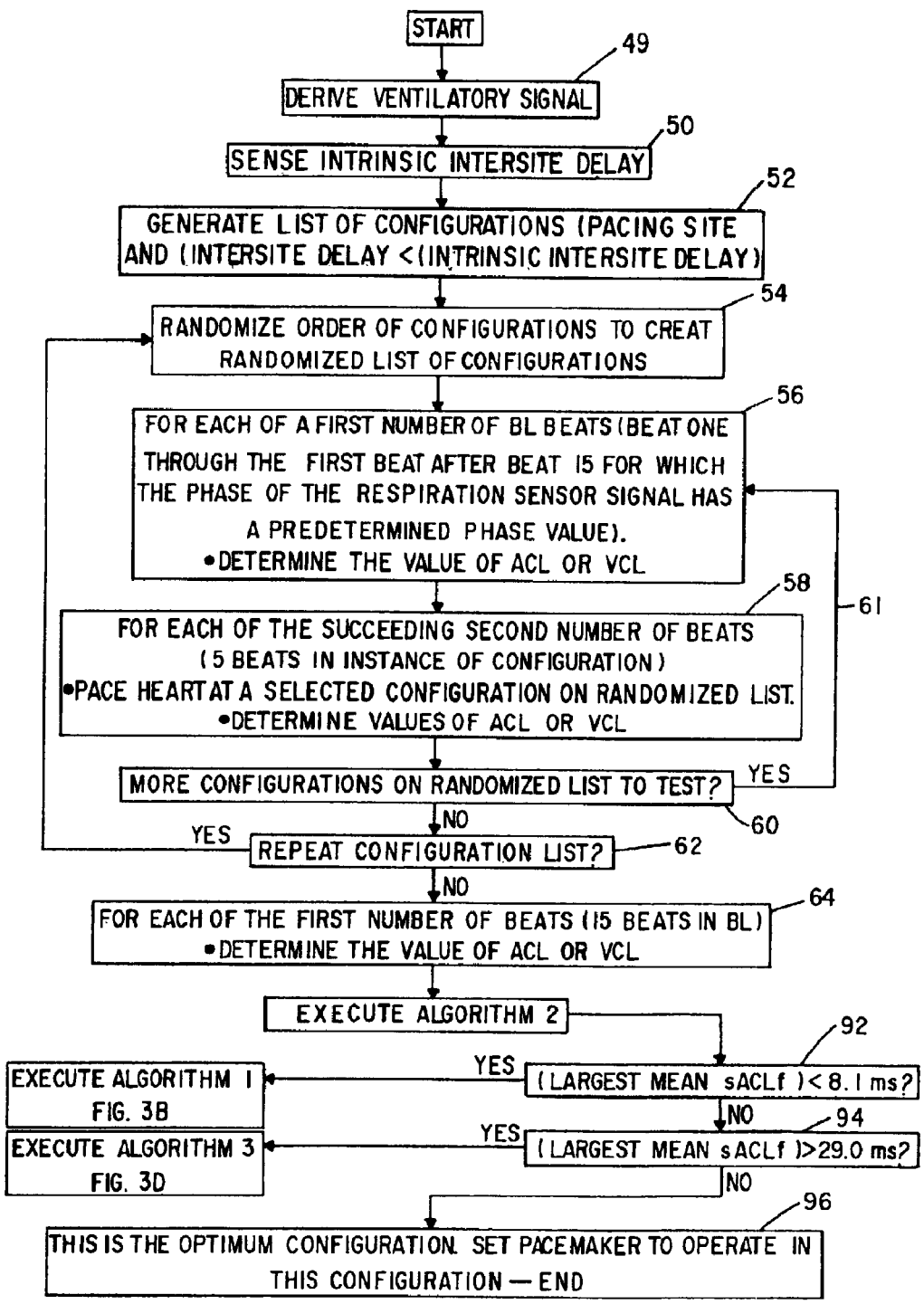

To avoid any influence that the particular order in which the configurations are employed in pacing the patient, the list generated in step 52 is randomized as reflected in block 54 in FIG. 3A.

Again, without limitation, a string of beats with the pulse generator inhibited may be used to establish BL and then for each of these baseline beats, the atrial cycle length between them is determined. As earlier mentioned, rather than using intrinsic cardiac rhythm to establish BL, the BL can also be at a particular paced rate and pacer site and intersite delay. In the description to follow, a group of at least 15 sequential beats are generated. The ACL measurement may be performed in the microprocessor by initiating a timer upon the occurrence of a P-wave in the cardiac electrogram and stopping the timer upon detection of the next succeeding P-wave. The ACL value associated with each BL beat is then stored as an array in the RAM memory 36.

In accordance with the present invention, the initiation of the transient beat series of each configuration of site and intersite delay value is synchronized to the ventilatory signal. As such, the first beat of a given transient series is initiated only after the first beat after beat 15 in creating the BL occurs following the ventilatory signal reaching a predetermined phase value, $\phi$. This relationship is illustrated in FIG. 6. At rest, a person normally breathes in and out about 16 times a minute. If that person's heart rate is 72 beats/minute, there are about 4½ beats per breathing cycle. The somewhat sinusoidal waveform 100 in FIG. 6 corresponds to the tidal volume variation over time where the rising portion of each wave corresponds to inspiration and the falling portion corresponds to expiration. Marked on the waveform 100 by dots are intrinsic heartbeats or possibly paced beats at a programmed baseline value of rate, site, and intersite delay value. Paced transient beats are indicated by a dot with a vertical line superimposed. As is indicated, 15 baseline beats are counted and then a determination is made as to whether the respiratory wave 100 has reached a predetermined phase, $\phi$. The series of five paced transient beats of a selected configuration are then initiated one beat following the time at which the predetermined phase $\phi$ is reached. After the fifth paced transient beat, intrinsic or baseline pacing is again resumed for another 15 beats, whereupon another series of paced transient beats of a second selected configuration is generated once the predetermined phase condition is met.

Referring again to the block diagram of FIG. 3A, immediately following the last of the beats used in establishing BL, the heart is paced using a selected configuration drawn from the randomized list developed at block 54. Again, without limitation, the second number of beats may equal five. As with the BL beats, the ACL for the paced beats is also determined as reflected in block 58.

A test is next made at block 60 to determine whether all of the 15 possible configurations on the randomized list have been used and the ACL values associated therewith stored in the memory.

If not all of the configuration possibilities have been exhausted, control returns over path 61 to block 56 and the operations reflected in blocks 56 and 58 are repeated until all of the possibilities have been exhausted. So that any anomalies which may have occurred in the measurement of the respective ACL values can be averaged out, steps 54, 56, 58 and 60 are repeated a predetermined number of times, e.g., five times, to obtain additional instances of the configurations that can later be averaged. See decision block 62.

The change in PP caused by the five paced beats in step 58 is immediate. There is no time delay. However, the change in ACL caused by the reflex mechanism of the Autonomic Nervous System in response to this change in PP is not immediate. There is a time delay of several beats. Thus, the delayed change in ACL can occur during the 15 BL beats in step 56 which follow the five paced beats in step 58. Thus, the final 15 or more BL beats in step 64 are needed to follow the final five paced beats in step 58.

Once the raw ACL values have been computed and stored as an array in the RAM memory, further algorithms may be used to process the raw data in arriving at the particular pacing site/intersite delay configuration yielding optimum hemodynamic performance.

Figure 3B:
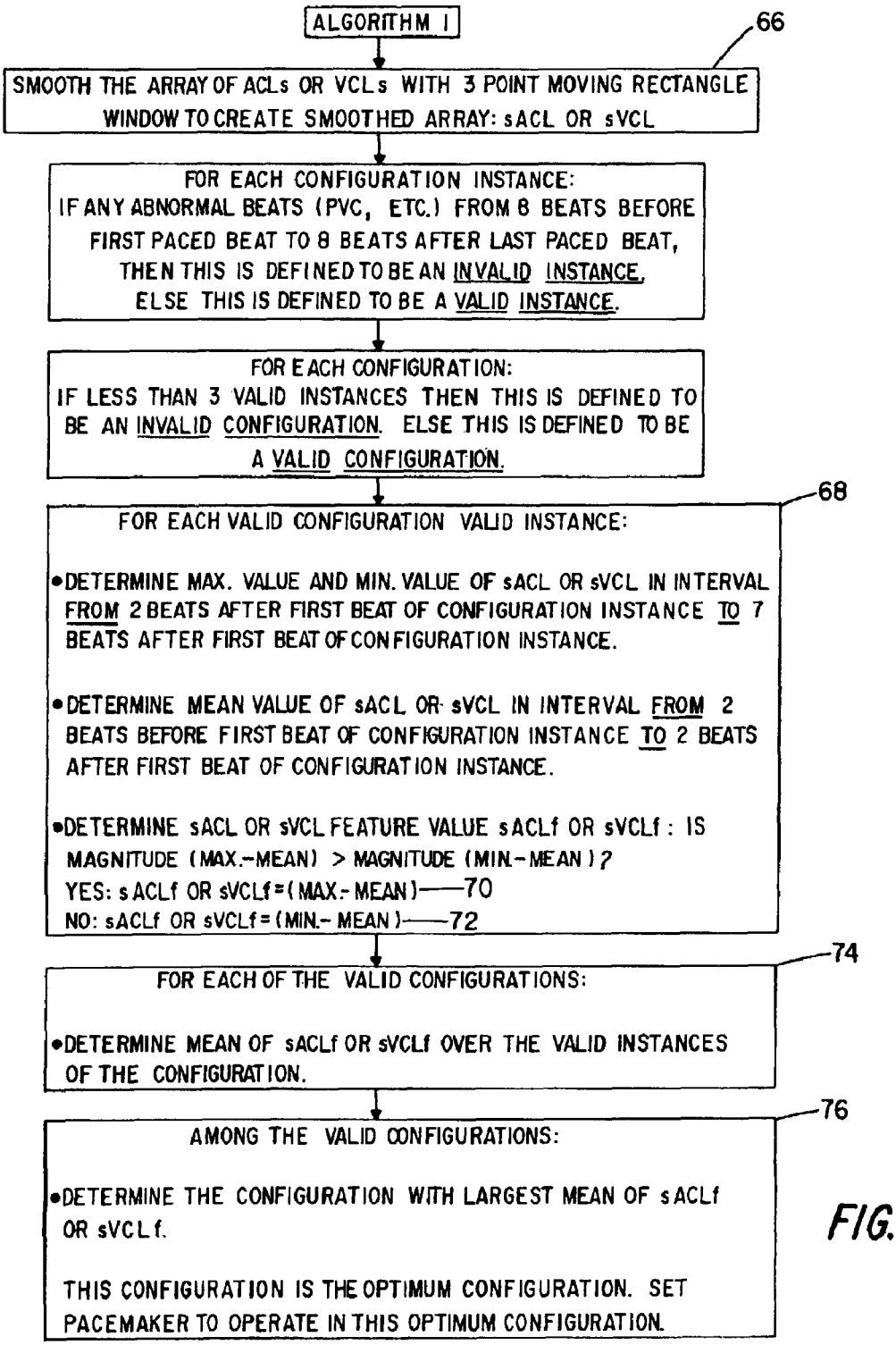
Figure 3C:
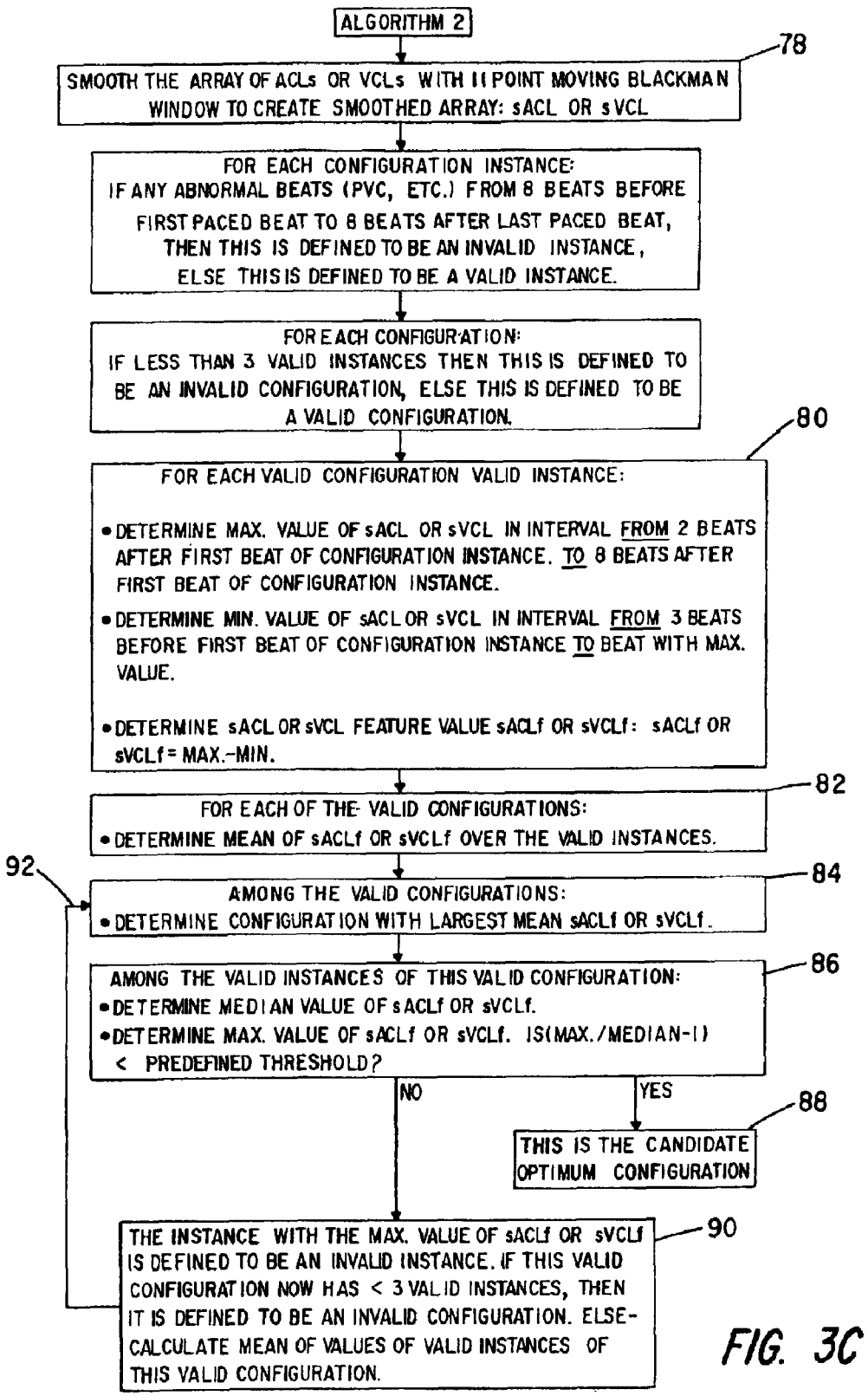

Algorithm 2 shown on FIG. 3C is executed to first select candidates for being the optimum configuration of pacing site and intersite delay. Here, the raw ACL data (or VCL data where VCL is the duration of the interval between consecutive R-waves in an ECG signal) are first smoothed using a known signal processing approach referred to as an 11 point moving Blackman window which yields a smoothed ACL array, sACL. At block 77, a determination is made as to whether any abnormal beats, e.g., PVCs, occurred during an interval from eight beats before the first transient pace beat to 8 beats after the last transient paced beat. If abnormal beats are detected, the collected data is defined to be an "invalid instance". If no such abnormal beats occurred, it is defined to be a "valid instance". Next, and as reflected by block 79, for each configuration, a determination is made as to whether less than three "valid instances" occurred and, if so, it is defined to be an "invalid configuration". On the other hand, if three or more valid instances occur, it is defined to be a "valid configuration".

Figure 5:
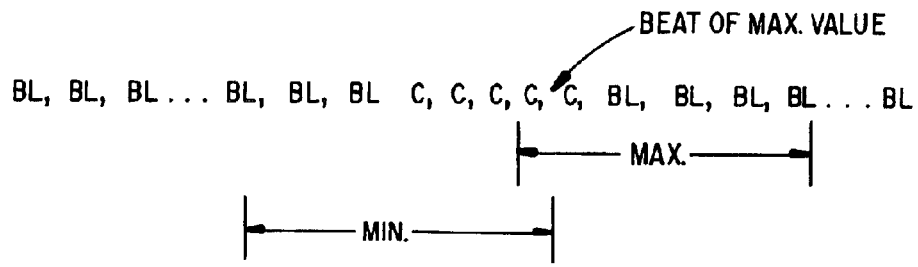
FIG. 5 is a drawing similar to FIG. 4 for a second algorithm.

Next, as indicated by block 80, for each valid instance of a valid configuration, a determination is made as to the maximum value of sACL values in an interval from two beats after the first beat of a configuration instance to eight beats after the first beat of the configuration instance. Likewise, a minimum value of sACL values in an interval from three beats before the first beat of the configuration instance to the beat with the maximum value is determined. FIG. 5 is helpful in defining the respective intervals in which the maximum values and minimum values are to be found. Once the maximum value and minimum value in the respective intervals have been determined, a smoothed ACL feature value, referred to in the flow charts by the acronym sACLf, is computed as the maximum value minus the minimum value.

Upon completion of step 80, for each of the valid configurations of site and intersite delay, the mean of the sACLf values over the number of valid instances of a given configuration is computed. See block 82. Next, out of the previously determined valid configurations, the configuration exhibiting the largest mean sACLf is computed (block 84).

Once the particular configuration exhibiting the largest mean sACLf is arrived at, via step 84, the valid instances where the particular valid configuration has been repeated are examined to determine a median value and a maximum value of the smoothed ACL feature, sACLf. With the median and maximum values so determined, a test is made to determine whether the quantity (MAX/MEDIAN−1) is less than a predefined threshold. The purpose of this threshold test is to remove a MAX whose value is too large (relative to the median value). The "predefined threshold" has been determined empirically from data accumulated from a significant number of patients as a value of 9.5, which gives good results for the set of patients investigated. If the result of the test is true, a potential candidate for the optimum configuration has been arrived at (block 88). However, if the test at block 86 had proved false, the instance with the maximum value of sACLf is defined to be an invalid instance. IF this valid configuration now has less than three valid instances, THEN it is defined to be an invalid configuration. If the valid configuration has three or more valid instances, the mean of values of valid instances is calculated for the valid configuration. Control then loops back over line 91 to block 84 to again repeat steps 84 and 86 until such time as the test set out in block 86 comes out "true".

Figure 3D:
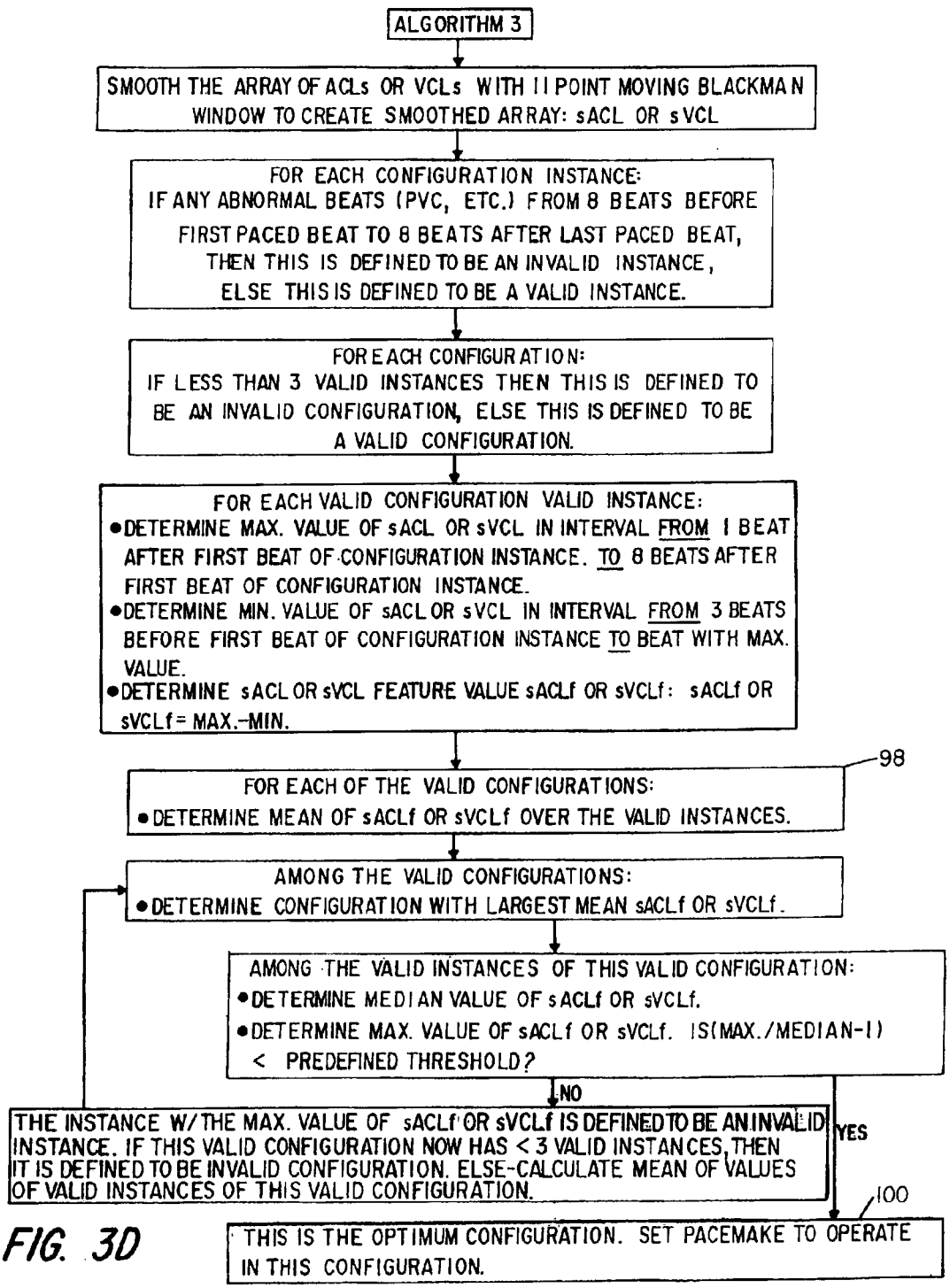

Referring again to the flow diagram of FIG. 3A, after all candidates for the optimum configuration have been determined, further processing takes place to determine which of the candidates is the optimum configuration so that the pacemaker can be programmed to operate in this configuration. Specifically, a test is made at block 92 to determine whether the largest mean sACLf computed at block 82 is less than 8.1 milliseconds. If it is, algorithm 1 of FIG. 3B is executed. If not, a further test is made to determine whether the largest mean sACLf value is greater than 29.0 milliseconds. If so, algorithm 3 illustrated at FIG. 3D is executed. If the largest mean sACLf feature value lies between 8.1 milliseconds and 29.0 milliseconds, it is the optimum configuration and, as indicated by block 96, the pacemaker is programmed to operate with that configuration of pacing site and intersite delay. The 8.1 ms and 29.0 ms values have been empirically established by study of data obtained from a set of ten patients in a study.

Referring next to FIG. 3B, the details of Algorithm 1 will be further explained. The first step in Algorithm 1 is identified by block 66 and involves smoothing the array of ACLs with a 3-point moving rectangle window. The resulting sACLf values are then also stored in the RAM memory. While other smoothing techniques are known to persons skilled in signal processing, a 3-point moving rectangle technique proves to be simple to execute and produces reliable results.

As was the case with algorithm 2, tests are made to determine whether any abnormal beats occurred in the interval from 8 beats before a first paced transient beat to 8 beats after the last paced transient beat for each of the configuration instances and if such an abnormal beat did occur, that configuration instance would be determined to be invalid. Then, each configuration is examined to determine if three or more valid instances were found in that configuration and, if so, it would be defined to be valid. However, if a configuration was found to include less than three valid instances, it would be defined as an invalid configuration.

Figure 4:
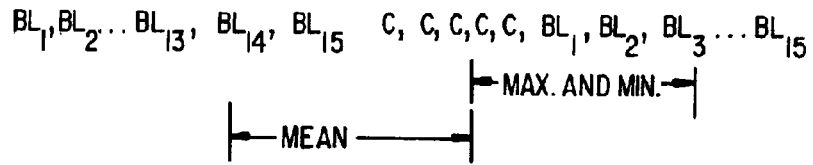
FIG. 4 is a representation of a series of baseline and paced beats useful in explaining the development of ACL features in accordance with a first algorithm.

Next, and as is reflected by block 68 in the flow diagram of FIG. 3B, for each valid instance of each valid configuration, the maximum value and the minimum value of the smooth ACL in an interval from two beats after the first beat of the configuration instance to seven beats after the first beat of the configuration instance are computed. This operation is further explained with the aid of FIG. 4. In FIG. 4, there is shown a series of 15 baseline beats, followed by five paced beats of an instance of a first configuration identified as $C_1$, again followed by another series of 15 baseline beats. The interval in which the maximum and minimum values of smoothed ACLs are to be located is labeled "MAX and MIN". Likewise, the interval in which the mean value of the smoothed ACLs is to be located is identified by "MEAN". By selecting the intervals in the manner indicated, changes in ACL of a transient nature as distinguished from steady state are guaranteed. Once the MAX and MIN values of sACL for the configuration instance have been arrived at, a test is made to determine whether the absolute value of the quantity (MAX−MEAN) is greater than the absolute value of the quantity (MIN−MEAN) for the configuration instance. If the outcome of the test is true, then the smoothed ACL feature (sACLf) for the configuration instance is determined to be the quantity (MAX−MEAN). If the test is false, then sACLf is made to be (MIN−MEAN). See steps 70 and 72 in block 68.

Next, as is indicated by operation block 74, for each of the valid configurations, a computation is made to determine the average or mean of the sACLf over the number of valid instances of that configuration. Once the operation indicated by block 74 has been completed, the particular valid configuration exhibiting the greatest mean of smoothed ACL features is identified, and the pacemaker is automatically programmed to operate with this optimum configuration. See block 76.

Referring again to FIG. 3A, if the test at block 94 had established that the largest mean sACLf had been greater than 29.0 milliseconds, algorithm 3 shown in FIG. 3D would have been executed rather than algorithm 1. Referring to FIG. 3D, the steps therein are substantially identical to those of algorithm 2 shown in FIG. 3C except that in block 98 of FIG. 3D corresponding to block 80 in FIG. 3C, the maximum value of sACL (or sVCL) is determined at an interval of from one beat after the first beat of a configuration instance rather than from two beats after the first beat of a configuration instance. Secondly, block 100 in algorithm 3 shown in FIG. 3D differs from block 88 of algorithm 2 shown in FIG. 3C in that rather than identifying a candidate optimum configuration, the actual optimum configuration is established and the pacemaker is then programmed to operate in this optimum configuration.

Patient tests have shown that the relatively easy-to-measure atrial cycle length (or ventricular cycle length) can be used to automatically determine the pacing site and intersite delay configuration which provides pulse pressures greater than the pulse pressure achieved with baseline cardiac performance. Thus, the need for a special sensor to actually measure pulse pressure itself, which is difficult to measure, is eliminated.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself.

As already mentioned, the intrinsic and paced beat information can readily be telemetered out to an external programmer/monitor incorporating a microprocessor and associated memory so that the ACL determinations and signal processing thereof can be done external to the patient in arriving at the optimal pacing site and intersite delay interval. While the foregoing description of a preferred embodiment has been described in the context of utilizing ACL as the measured parameter for assessing the efficacy of the pacing site and intersite delay parameters, those skilled in the art will recognize that parameters other than ACL may also be used. Such other parameters may include but are not necessarily limited to blood flow parameters measurable using Doppler techniques, total acoustic noise measured using accelerometer sensors, stroke volume, cardiac output and derivatives thereof using impedance plethysmography as described in U.S. Pat. No. 4,686,987 to Salo, which is hereby incorporated by reference. It is further contemplated that ventricular pressure may serve as the optimized performance parameter and in this event a piezoelectric pressure transducer may be disposed on a right or left ventricular pacing lead where it is then used to measure right or left ventricular pressure parameters, such as end-diastolic or end-systolic pressure which correlate closely to ventricular contractility. Hence, the scope of the invention is to be determined from the appended claims.

What is claimed is:

1. A method of optimizing the site and intersite delay configuration of a dual chamber pacemaker of the type having means for sensing atrial depolarization events, means for sensing ventricular depolarization events and means for applying cardiac stimulating pulses selectively to the right, left or both ventricular chambers at predetermined intersite intervals following detection of atrial depolarization events, comprising the steps of:

(a) tracking a patient's intrinsic atrial depolarization events;

(b) deriving from a transthoracic impedance signal a cyclic respiratory signal representative of a patient's tidal volume;

(c) measuring the patient's cycle length between successive depolarization events over a first predetermined number of heart beats, $N_1$, at a first intersite interval and storing the measured cycle lengths as an array in a memory to establish a baseline value;

(d) changing at least one of intersite delay interval and pacing site configuration by changing, for a second predetermined number of heart beats, $N_2$, less than the first predetermined number of heart beats, (i) the intersite delay interval of the pacemaker from the baseline value to a different intersite delay interval less than the value at which intrinsic atrial depolarization is established, or (ii) the site(s) of the ventricle(s) to which the stimulating pulses are applied;

(e) measuring the patient's cycle length between successive atrial depolarization events over the second predetermined number of heart beats and storing the measured cycle lengths in the array in said memory;

(f) calculating and storing a cycle length feature value obtained from the patient's cycle length measured in steps (c) and (e);

(g) repeating steps (a)–(f) in iterative cycles over a range of intersite delay intervals and ventricular chamber(s)

selected for receiving the cardiac stimulating pulses where the second predetermined number of beats, $N_2$, for each iterative cycle begins at a corresponding phase of the said cyclic respiratory signal;

(h) after step (f) for each pacing site and intersite delay configuration, calculating the average of the cycle length features over all of the occurrences of the configuration;

(i) determining the optimal configuration from among the averages determined in step (g); and (j) setting the intersite delay and pacing site configuration of the pacemaker to the optimal intersite delay and pacing site configuration established in step (i).

2. The method of claim 1 wherein an atrial cycle length (ACL) feature value is calculated by the steps of:

(k) smoothing the array of cycle lengths;

(l) determining from the smoothed array of ACLs a maximum value and a minimum value in a first predetermined interval measured in beats for each intersite delay and pacing site configuration;

(m) determining from the smoothed array a mean value of cycle lengths in a second predetermined interval measured in beats for each intersite delay and pacing site configuration;

(n) computing an absolute value of the difference between said maximum value and said mean value and computing an absolute value of the difference between said minimum value and said mean value;

(o) comparing the absolute value of the difference between the maximum value and the mean value with the absolute value of the difference between the minimum value and the mean value to determine which is the larger; and (p) setting the cycle length feature value to the difference between the maximum value and the mean value when the absolute value of that difference is greater than the absolute value of the difference between the minimum value and the mean value, and setting the cycle length feature value to the difference between the minimum value and the mean value when the absolute value of the difference between the maximum value and the mean value is less than or equal to the absolute value of the difference between the minimum value and the mean value.

3. A method for optimizing the intersite delay interval and pacing site configuration of a programmable dual chamber cardiac pacemaker of the type having means for sensing atrial and ventricular depolarization events, including a microprocessor-based controller for selectively stimulating the right, the left or both ventricular chambers with pacing pulses at predetermined intersite delay intervals following detection of atrial depolarization events, the microprocessor-based controller having means for determining atrial cycle lengths and a memory for storing data in an addressable array, comprising the steps of:

(a) deriving a cyclic respiratory signal corresponding to a patient's tidal volume from a transthoracic impedance signal;

(b) storing in the memory a listing of pacing site and intersite delay configurations, each such configuration specifying ventricular chamber(s) to be stimulated and an intersite delay interval to be utilized;

(c) pacing the ventricular chamber(s) in accordance with a pacing site intersite delay configuration selected randomly from said listing for a first number of beats, $N_1$, following a second number of intrinsic beats, $N_2$, sufficient to establish a base line;

(d) repeating step (c) where the first number of beats, $N_1$, begin at a same phase in the cyclic respiratory signal, for each pacing site and intersite delay configuration contained in the listing;

(e) determining the atrial cycle length (ACL) values between each of the $N_1$ and $N_2$ beats resulting from steps (b) and (c) and storing said ACL value in the addressable array in the memory;

(f) repeating steps (b) through (d) a predetermined number of instances, $N_3$;

(g) smoothing the array of ACLs;

(h) determining for all $N_3$ instances of each pacing site and intersite delay configuration the maximum value of the smoothed ACLs in a first interval beginning after a change to the first number of beats $N_1$ and ending after a change to the second number of beats, $N_2$, and a minimum value of the smoothed ACLs in a second interval beginning a predetermined number of beats prior to a change from the $N_2$ beats to the $N_1$ beats and ending with the beat associated with the maximum value;

(i) computing a smoothed ACL feature as the difference between the maximum value and the minimum value;

(j) calculating the mean value of the smoothed ACL features computed in step (h) over the $N_3$ instances for each pacing site and intersite delay configuration and determining the configuration yielding the largest mean value;

(k) determining among the $N_3$ instances associated with the configuration yielding the largest mean value a median value and a maximum value of smoothed ACL features; and (l) programming the pacemaker to the configuration determined in step (j) when the difference between the ratio of maximum value and the median value is less than a predetermined value.

4. The method of claim 3 and when the ratio of maximum value and the median value of smoothed ACL features is greater than or equal to the predetermined threshold value, repeating steps (j) and (k) after recalculating the mean of the instances of the configuration associated with the largest mean value of smoothed ACL features after removing the instance having the maximum value of smoothed ACL features from the instances.

5. A method of optimizing the intersite delay and pacing site configuration of a dual chamber pacemaker of the type having means for sensing atrial depolarization events, means for sensing ventricular depolarization events and means for applying cardiac stimulating pulses selectively to the right, left or both ventricular chambers at predetermined intersite delay intervals following detection of atrial depolarization events, comprising the steps of:

(a) tracking a patient's intrinsic ventricular depolarization events;

(b) deriving from a sensed transthoracic impedance signal a cyclic signal related to a patient's tidal volume;

(c) measuring the patient's ventricular cycle length (VCL) between successive ventricular depolarization events over a first predetermined number of heart beats, $N_1$, at a first intersite delay interval and storing the measured VCLs as an array in a memory to establish a baseline value;

(d) changing at least one of intersite delay interval and pacing site configuration by changing, for a second predetermined number of heart beats, $N_2$, less than the first predetermined number of heart beats,
  (i) the intersite delay interval of the pacemaker from the baseline value to a different intersite delay interval less than the value at which intrinsic ventricular depolarization events is established;
  (ii) the ventricular sites to which the stimulating pulses are applied;
(e) measuring the patient's VCLs between successive ventricular depolarization events over the second predetermined number of heart beats and storing the measured VCLs in the array in said memory;
(f) calculating and storing a VCL feature value obtained from the patient's ventricular cycle length measured in steps (b) and (d);
(g) repeating steps (a)–(f) in iterative cycles over a range of intersite delay intervals and ventricular sites selected for receiving the cardiac stimulating pulses where the second predetermined number of beats, $N_2$, for each iterative cycle begins at a corresponding phase of said cyclic signal;
(h) after step (g) for each pacing site and intersite delay configuration, calculating the average of the VCL features over all of the occurrences of the configuration;
(i) determining the optimal configuration from among the averages determined in step (h); and
(j) setting the intersite delay and pacing site configuration of the pacemaker to the optimal delay and pacing site configuration established in step (i).

6. The method of claim 5 wherein the VCL feature value is calculated by the steps of:
(k) smoothing the array of VCLs;
(l) determining from the smoothed array of VCLs a maximum value and a minimum value in a first predetermined interval measured in beats for each intersite delay and pacing site configuration;
(m) determining from the smoothed array a mean value of VCLs in a second predetermined interval measured in beats for each intersite delay and pacing site configuration;
(n) computing an absolute value of the difference between said maximum value and said mean value and computing an absolute value of the difference between said minimum value and said mean value;
(o) comparing the absolute value of the difference between the maximum value and the mean value with the absolute value of the difference between the minimum value and the mean value to determine which is the larger; and
(p) setting the VCL feature value to the difference between the maximum value and the mean value when the absolute value of that difference is greater than the absolute value of the difference between the minimum value and the mean value, and setting the VCL feature value to the difference between the minimum value and the mean value when the absolute value of the difference between the maximum value and the mean value is less than or equal to the absolute value of the difference between the minimum value and the mean value.

7. A method for optimizing the intersite delay interval and pacing site configuration of a programmable, dual-chamber, cardiac pacemaker of the type having means for sensing atrial and ventricular depolarization events, including a microprocessor-based controller for selectively stimulating the right, the left or both ventricular chambers with pacing pulses at predetermined intersite delay intervals following detection of atrial depolarization events, the microprocessor-based controller having means for determining ventricular cycle lengths (VCLs) and a memory for storing data in an addressable array, comprising the steps of:
(a) deriving a cyclic signal corresponding to a patient's tidal volume;
(b) storing in the memory a listing of pacing site and intersite delay configurations, each such configuration specifying ventricular sites to be stimulated and an intersite delay interval to be utilized;
(c) pacing the ventricular sites in accordance with a pacing site and intersite delay configuration selected randomly from said listing for a first number of beats, $N_1$, following a second number of intrinsic beats, $N_2$, sufficient to establish a baseline;
(d) repeating step (c) for each pacing site and intersite delay configuration contained in the listing where the first number of beats, $N_1$, on successive iterations begins at the same phase in the cyclic signal;
(e) determining the VCL values between each of the $N_1$ and $N_2$ beats resulting from steps (c) and (d) and storing said VCL value in the addressable array in the memory;
(f) repeating steps (c) through (e) a predetermined number of instances, $N_3$;
(g) smoothing the array of VCLs;
(h) determining for all $N_3$ instances of each pacing site and intersite delay configuration the maximum value of the smoothed VCLs in a first interval beginning after a change to the first number of beats, $N_1$, and ending after a change to the second number of beats, $N_2$, and a minimum value of the smoothed VCLs in a second interval beginning a predetermined number of beats prior to a change from the $N_2$ beats to the $N_1$ beats and ending with the beat associated with the maximum value;
(i) computing a smoothed VCL feature as the difference between the maximum value and the minimum value;
(j) calculating the mean value of the smoothed VCL features computed in step (i) over the $N_3$ instances for each pacing site and intersite delay configuration and determining the configuration yielding the largest mean value;
(k) determining among the $N_3$ instances associated with the configuration yielding the largest mean value a median value and a maximum value of smoothed VCL feature; and
(l) programming the pacemaker to the configuration determined in step (j) when the difference between the ratio of maximum value and the minimum value is less than a predetermined value.

8. The method of claim 7 and when the ratio of maximum value and the median value of smoothed VCL features is greater than or equal to the predetermined threshold value, repeating steps (j) and (k) after recalculating the mean of the instances of the configuration associated with the largest mean value of smoothed VCL features after removing the instance having the maximum value of smoothed VCL features from the instances.

9. A method for optimizing the intersite delay interval and pacing site configuration of a cardiac pacemaker comprising the steps of:
(a) deriving a cyclic signal corresponding to a patient's tidal volume, (b) selecting a first of a plurality of predetermined pacing site and intersite delay interval configuration;

(c) establishing a baseline value of intrinsic intersite intervals over a predetermined number of intrinsic heart beats;

(d) initiating pacing of the patient's heart with the first of the plurality of predetermined pacing site and intersite delay interval configurations for a predetermined number of paced beats;

(e) repeating step (c); and (f) repeating step (d) with a second of the plurality of predetermined pacing site and intersite delay interval configurations where a first pacing pulse of the predetermined number of paced beats begins at a same phase of the cyclic signal as a first pacing pulse of the predetermined number of paced beats used in step (d).

* * * * *